United States Patent
Nallakrishnan

Patent Number: 5,431,671
Date of Patent: Jul. 11, 1995

[54] SURGICAL KNIFE WITH RETRACTABLE AND ANGULARLY ADJUSTABLE BLADE

[76] Inventor: Ravi Nallakrishnan, 26 Plaza Dr., Westmont, Ill. 60559

[21] Appl. No.: 69,266

[22] Filed: May 28, 1993

[51] Int. Cl.⁶ .............................................. A61B 17/32
[52] U.S. Cl. .................................... 606/167; 30/162; 30/321; 606/166
[58] Field of Search ............... 606/166, 167, 170, 172; 30/89, 151, 155, 162, 320, 321

[56] References Cited

U.S. PATENT DOCUMENTS

| | | | |
|---|---|---|---|
| 3,176,395 | 4/1965 | Warner et al. | 30/162 |
| 3,609,864 | 10/1971 | Bassett | 30/321 |
| 3,922,784 | 12/1975 | Prince et al. | 30/321 |
| 4,100,677 | 7/1978 | Jeff | 30/321 |
| 4,499,898 | 2/1985 | Knepshield et al. | 606/167 |
| 4,516,575 | 5/1985 | Gerhard et al. | 606/167 |
| 4,672,964 | 6/1987 | Dee et al. | 606/167 |
| 4,788,976 | 12/1988 | Dee | 606/167 |
| 4,802,279 | 2/1989 | Rowe | 30/151 |
| 4,898,170 | 2/1990 | Hofmann et al. | 606/166 |
| 5,055,106 | 10/1991 | Lungren | 606/167 |

FOREIGN PATENT DOCUMENTS 2113550  8/1983  United Kingdom ................ 606/166

*Primary Examiner*—Ralph A. Lewis
*Attorney, Agent, or Firm*—Jerry A. Schulman

[57] ABSTRACT

A surgical knife intended for use in ophthalmic surgery has a blade which is angularly adjustable with respect to the knife handle without requiring removal of the blade or adjustment of mechanical elements such as clamps, screws, levers, locks or the like. The blade can be retracted into the knife handle to protect the blade from damage between uses, and to protect against accidental cuts.

9 Claims, 2 Drawing Sheets

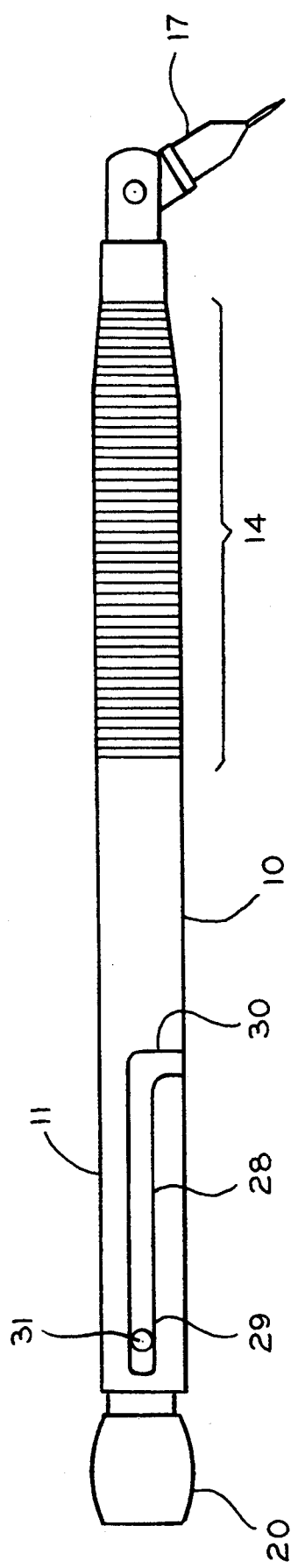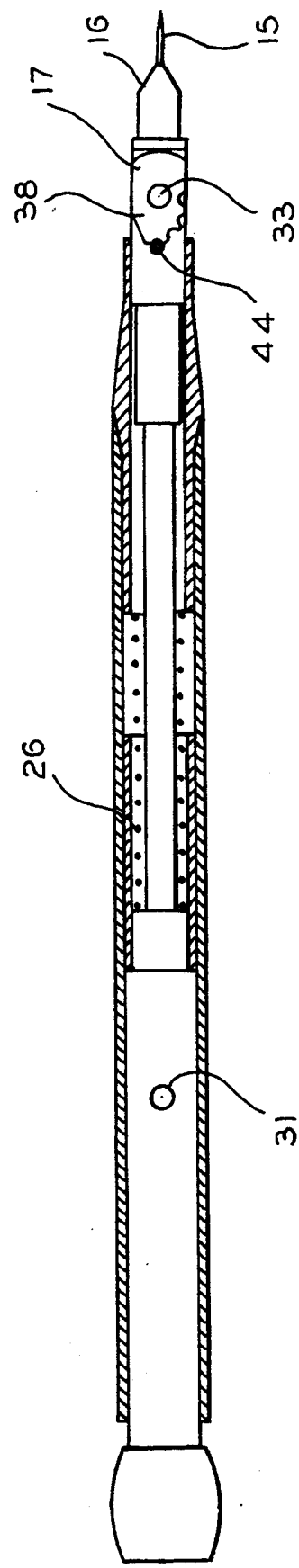

SURGICAL KNIFE WITH RETRACTABLE AND ANGULARLY ADJUSTABLE BLADE

This invention relates generally to surgical knives and, more particularly, to knives for ophthalmic surgery with blades that are angularly adjustable during surgery and that retract into the knife handle between uses.

BACKGROUND OF THE INVENTION

Ophthalmic surgeons work within a very small operating field upon organs whose tissues are complex and delicate. Cuts made during surgery must be precise as to length, direction and depth, requiring surgical knives of unsurpassed sharpness and maneuverability.

Heretofore, most surgical knives available had blades held in fixed, non-adjustable relationship to the knife handle. Some blades were offset at a selected angle, while most blades extended straight out from the handle. Blades could be made with different configurations for particular cuts, but once these cuts were made, a new blade (or a new knife) had to be substituted for the remainder of the surgery.

Others have developed surgical knives with blades or blade holders that are angularly adjustable.

U.S. Pat. No. 4,672,964 (Dee) describes and claims a knife having a blade holder with a ball formed on one end which fits rotatably into a socket formed on a housing which then, in turn, is threadably attached to a knife handle. Mounted on the handle is a crank lever which moves a push rod toward the socket to contact the ball (and fix it in a selected position), or moves the push rod away from the ball to enable the ball (and, thereby, the blade holder) to rotate with respect to the handle. Changing the angle of the blade is an involved procedure: the surgeon must hold the handle with one hand and release the ball with the other by lifting the lever, reorient the blade, and re-clamp the ball by lowering the lever.

U.S. Pat. No. 4,788,976 (Dee, et al.) is a continuation-in-part of the '964 Dee patent, and adds to the '964 Dee patent a modified version of the crank lever mechanism used to clamp the ball and lock the blade in a selected position. Changing the blade angle still calls for significant manipulation of the knife adjusting mechanism.

U.S. Pat. No. 3,609,864 (Bassett) teaches and describes a surgical blade handle with a blade holder mounted to a ball. A knurled knob is threaded into the end of the handle, and a push rod extends within the handle from the knob to the ball. When the knob is threaded into the handle, the push rod contacts and clamps the ball at a selected angle, a two-handed procedure.

An arrangement very similar to that of Bassett is shown in Swiss patent 490,072 (Muller). A blade-and-ball assembly fits into a socket in a blade holder, and a handle is threaded into the blade holder until a handle projection contacts the ball.

U.S. Pat. No. 4,275,735 (Chutter) teaches and describes a blade holder within which a surgical blade may be selectively oriented and clamped. There is no capability for changing the angle of the blade during an operation without disassembling the holder and reinserting the blade. It appears that Chutter contemplates the prior setup of the knife rather than "on-the-fly" changes that may be required during surgery.

U.S. Pat. No. 3,922,784 (Prince, et al.) teaches and describes a swivel knife consisting of a handle and a blade holder clamped to the end of the handle. The blade holder allows the blade to be rotated about the axis of the blade holder, and the angle at which the blade holder is "skewed" with respect to the handle may be changed by loosening and retightening a thumb screw.

None of the prior art adjusting mechanisms described above allow the knife blade to be withdrawn into the handle to protect the blade when the knife is not being used, and to protect against accidental cuts to one who picks up the knife. It is particularly important to prevent accidental cuts during surgery, or accidental perforation of surgical gloves, where the danger of contamination in a bloody operating field is present.

The need exists, then, for a knife particularly suited to ophthalmic surgery with a blade that is angularly adjustable without the operation of mechanical locks or levers, or the removal and reinstallation of the cutting blade.

The need also exists for a blade angularly adjustable to selected, discrete angular positions.

The need also exists for a blade adjustment mechanism which holds the blade with a force firm enough to allow use in surgery, yet allows simple, one-handed adjustment of the blade angle during surgery.

The need also exists for a blade adjusting mechanism that will allow the blade to be moved simply to a straight position and then to be withdrawn into the knife handle when not in use to protect the blade and to prevent accidental cuts to one picking up the knife.

BRIEF DESCRIPTION OF THE DRAWINGS

These and further aspects of the present invention will become more apparent upon consideration of the accompanying drawings, in which:

FIG. 1 is a top plan view showing the present invention showing the knife blade in the extended position;

FIG. 2 is a sectional view taken along line 2—2 of FIG. 1;

DETAILED DESCRIPTION OF THE DRAWINGS

Figure 3:
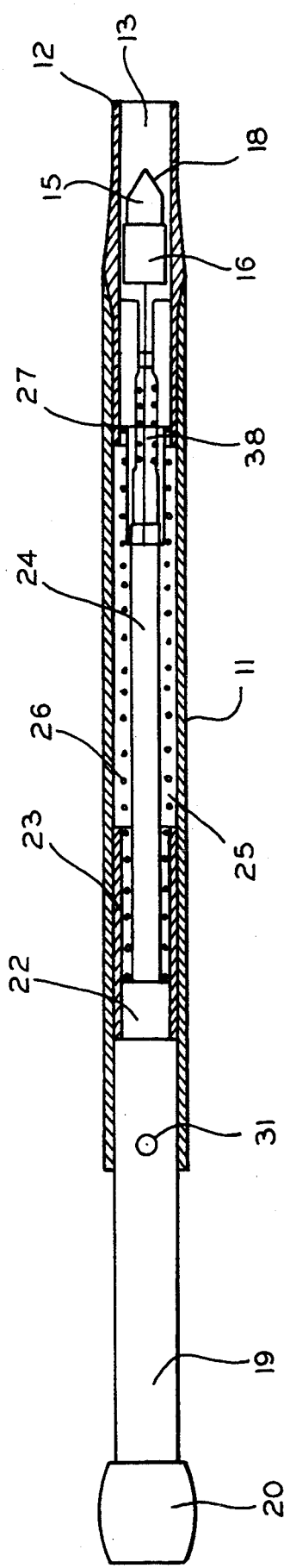
FIG. 3 is a sectional view taken along line 3—3 of FIG. 1, showing the knife blade in its non-extended position.

While the present invention is described herein within the context of ophthalmic surgery, it is to be understood that other uses for the invention are contemplated as well.

Referring now to FIG. 1, the numeral 10 indicates generally a surgical knife, typically of the type used during ophthalmic surgery. Knife 10 has a generally hollow, tubular case 11 with a tapered case tip 12 which terminates in a generally circular case mouth 13. Ridges are formed along a portion of case 11 and tip 12 to form a handgrip 14.

A preferred cutting element is a diamond blade 15, shown mounted in a bladeholder 16. In a preferred embodiment of the invention, bladeholder 16 is rotatably mounted to mounting block 17 in a manner to be more fully set forth herein. Blade 15 is formed with a series of cutting edges 18 which, in a preferred embodiment, is particularly useful for ophthalmic surgery.

Because the tissues to be cut during ophthalmic surgery are delicate and somewhat flexible, it is critical that edges 18 be extremely sharp and free from nicks. Keeping the edges so sharp also increases the risk of accidental cuts, particularly to the user's hands and to surgical gloves worn by users. It is a decided advantage to incorporate into such a surgical knife a means to protect the blade when the knife is not being used or is being retrieved prior to actual cutting. Accordingly, blade holder 16 is attached to mounting block 17 which, in turn, is selectably retractable into case 11, in a manner to be set forth more fully below. The user may then choose between the retracted blade position shown in FIG. 3 or the extended position shown in FIGS. 1 and 2.

Referring to FIG. 2, it can be seen that knife 10 has a cylindrical handle 19 sized and shaped to be concentric and coaxial with case 11 and to fit closely within and slide into and out of case 11. At its outermost end, handle 19 has a knob 20 attached thereto, and at its innermost end, a cylindrical collar assembly 21. Collar assembly 21 consists of a solid plug 22 from which a cylindrical skirt 23 extends in a direction toward tip 12.

A cylindrical plunger 24 is attached at one end to plug 22 and extends therefrom toward tip 12, and mounting block 17 is attached to the remaining end thereof. Plunger 24 is sized and shaped to create and define an annular cavity 25 between the outer surface of plunger 24 and the inner surface of skirt 23. A cylindrical coil plunger spring 26, sized to have a diameter larger than that of plunger 24 and smaller than that of skirt 23, has one end nested within cavity 25 and extends along the length of plunger 24 to abut shoulder 27 formed within case 11.

Spring 26 is compressed as handle 19 is moved into case 11; when handle 17 is released, spring 26 returns to its unstressed position forcing handle 19 out of case 11. Thus, spring 26 is compressed as plunger 24 and, thereby, mounting block 17 and blade 15, are extended from tip 12. Similarly, as handle 19 is released, spring 26 acts to withdraw mounting block 17 and blade 15 into case 11.

FIG. 1 demonstrates a preferred manner in which to lock blade 15 in an extended position. A locking slot 28 is formed as a generally J-shaped channel in case 11, with an axially-extending slot segment 29 and a circumferentially-extending foot segment or retaining bend 30. In FIG. 2, there is shown a locking peg 31 attached to and extending outward from handle 19. Peg 31 is positioned to register with slot 28 when knife 10 is assembled. Pushing knob 20 inward causes peg 31 to travel along axial slot segment 29 while spring 26 is being compressed and blade 15 is being extended from tip 12. As peg 31 reaches the end of axial segment 29, knob 20 is rotated to move peg 31 into foot segment 30, and as knob 21 is released, spring 26 causes peg 31 to push against and frictionally engage case 11 within foot segment 30, thus preventing blade 15 from being withdrawn into case 11. Twisting peg 20 to move knob 31 back into alignment with axial segment 29 allows blade 15 to be drawn back into case 11.

Figure 4:
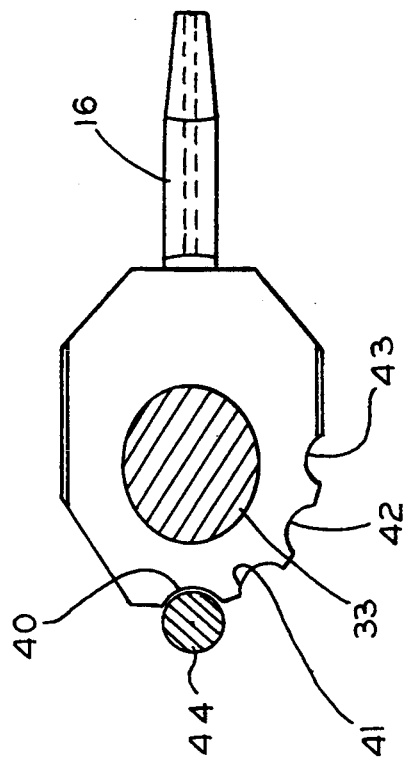
FIG. 4 is a partial sectional view along line 4—4 of FIG. 3 of the adjusting mechanism showing the sector plate.

Referring now to FIG. 4, a blade angle adjusting assembly is shown. A sector plate 38 is pivotally attached to mounting block 17 by pivot pin 33. Mounting block 17 is split at one end to form legs 34 and 35. Each leg has a mounting hole (36 and 37, respectively) positioned to allow pivot pin 33 to pass therethrough. As seen in FIG. 4, bladeholder 16 is mounted to mounting block 17 by aligning mounting hole 39 on sector plate 38 with holes 36 and 37, and passing pivot pin 33 therethrough.

Figure 5:
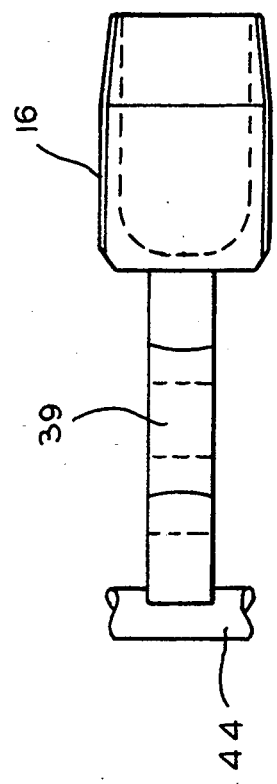
FIG. 5 is a top view of the sector plate and blade holder.

As seen in FIGS. 3 and 5, a retaining post 44 extends between and is attached to mounting block legs 34 and 35, and is positioned to engage said detents as sector plate 38 is rotated.

To adjust the angle of blade 15, bladeholder 16 is pivoted by rotating sector plate 38 about pivot pin 33. Throughout the arc of rotation, sector plate 38 contacts retaining post 44, bringing detents 40, 41, 42 and 43 into engagement, seriatim, with retaining post 44. Bladeholder 16 and, thereby, blade 15, are held at preselected, discrete angles of rotation by the interengagement of detents 40, 41, 42 and 43 with retaining post 44. The detents, as shown, are formed as arcuate grooves or cutouts to give the interengagement with cylindrical retaining post 44 a smoother and more cam-like action, allowing the angle of blade 15 to be changed with a minimum of manual effort. Other shapes for said detents and said retaining post, or selected surface finishes can be used to affect the degree of ease or difficulty with which the angle of blade 15 may be adjusted. The preferred embodiment presented herein contemplates the use of relatively smooth finishes on both sector plate and retaining pin, and the use of a cylindrical retaining pin.

Use of the present invention can be described as follows. Knife 10 is held with one hand at grip 14, while knob 20 is gripped with the other hand and pushed toward tip 12, moving plunger 24 with respect to case 11, causing locking peg 31 to travel along locking slot 28 while, at the same time, compressing return spring 26. When peg 31 reaches the end of its travel, peg 20 is then twisted to seat knob 31 in foot segment 30, holding plunger 24 in its extended position to expose blade 15, blade holder 16 and a portion of mounting block 17.

Blade 15 may then be set at a desired angle by pressing on bladeholder 16 with sufficient force to overcome the frictional engagement of retaining post 44 with one of detents 40, 41, 42 and 43, an operation that can be carried out as many times as found to be necessary or desirable during surgery.

Engagement with detent 40 holds bladeholder 16 and, thereby, blade 15 in a "straight" position, that is, with blade 15 aligned with the axis of case 11. Engagement with detent 43 orients blade 15 at approximately right angles to the axis of case 11. The machining and positioning of said detents is done to allow blade 15 to be held at preselected angles found to be advantageous for surgery.

To protect the blade 15, it must first be adjusted to the "straight" position before being retracted. Thereafter, knob 20 is twisted to move peg 31 from foot segment 30 back into alignment with axial slot 29, thus allowing spring 26 to push plunger 24 rearward, retracting blade 15 into case 11 via mouth 13.

While the foregoing has described certain preferred embodiments of the present invention, it is to be understood that these descriptions are by way of example only and are not intended to limit the allowable scope of the invention. It is expected that others will perceive variations which, while differing from the foregoing, do not depart from the spirit and scope of the invention herein described and claimed.

What is claimed is:

1. A surgical knife, said knife comprising:
   a hollow, tubular handle open at a first end thereof;
   a plunger assembly telescopically disposed within said handle;
   means for extending and retracting a first end of said plunger assembly from and into said handle via said first handle end;
   means for pivotally mounting a surgical cutting blade to said plunger proximate said first plunger end; and
   means for adjusting the angle of said cutting blade with respect to said handle and for retaining said blade at said angle by manually pushing directly against said cutting blade to move said blade from one discrete, preselected position to another.

2. A surgical knife, said knife comprising:
   a handle assembly,
   said handle assembly including a hollow, tubular handle open at a first end thereof,
   a plunger telescopically disposed within said handle;
   means for extending and retracting a first end of said plunger from and into said handle via said first handle end;
   means for pivotally mounting a surgical cutting blade to said plunger proximate said first plunger end;
   means for adjusting the angle of said cutting blade with respect to said handle assembly,
   said adjusting means attached to said plunger proximate said first plunger end whereby said adjusting means and, thereby, said blade, can be withdrawn into and extended from said handle, said angle adjusting mean; includes a series of detentes formed on said mounting means and a retaining pin attached to said plunger assembly and positioned to frictionally engage each of said detentes as said cutting blade is pivoted, to retain said blade at a selected angle with respect to said handle assembly, and
   means for selectively retaining said first plunger end in an extended position.

3. The apparatus as recited in claim 2 wherein said blade mounting means is pivotally attached to said plunger proximate said first plunger end, and said retaining pin is attached to said plunger and positioned to engage said detents.

4. The apparatus as recited in claim 2 wherein said retaining means includes an axially-extending channel formed through a wall of said handle and a peg which extends through said channel and is attached to said plunger whereby said peg may be moved along said channel to retract or extend said plunger into or from said handle, and
   a retaining bend formed in said channel to engage said peg and restrain said peg and, thereby, said plunger from moving.

5. The apparatus as recited in claim 4 wherein said extending and retracting means includes means for biasing said plunger to retract said plunger into said handle,
   said biasing means thereby seating said peg in said retaining bend.

6. The apparatus as recited in claim 2 wherein said adjusting means includes a blade holder constructed to grip and hold said cutting blade,
   said detents formed on said blade holder.

7. A surgical knife of the type having a surgical cutting blade, said knife comprising:
   a hollow knife handle;
   a plunger telescopically disposed within said handle;
   means for extending and retracting a first end of said plunger from and into said handle;
   means for pivotally mounting said cutting blade to said first plunger end;
   means for adjusting the angle of said cutting blade with respect to said handle,
   said adjusting means including a series of detents formed on said blade mounting means and a retaining pin positioned to frictionally engage each of said detents as said mounting means is pivoted; and
   means for retaining said plunger in an extended position to expose said cutting blade.

8. The apparatus as recited in claim 7 wherein said retaining means includes an axially-extending channel formed through a wall of said handle and a peg which extends through said channel and is attached to said plunger whereby said peg may be moved along said channel to retract or extend said plunger from said handle, and
   a retaining bend formed in said channel to engage said peg and restrain said knob, and, thereby, said plunger from moving.

9. The apparatus as recited in claim 8 wherein said extending and retracting means includes means for biasing said plunger to retract said plunger into said handle,
   said biasing means thereby forcing said peg to be held in said retaining bend.

* * * * *